(12) United States Patent
Williams et al.

(10) Patent No.: US 8,772,354 B2
(45) Date of Patent: Jul. 8, 2014

(54) MALODOR COUNTERACTING COMPOSITIONS AND METHOD FOR THEIR USE

(75) Inventors: Jonathan Williams, London (GB); Lyse Tranzeat, West Drayton (GB)

(73) Assignee: Firmenich SA, Geneva (CH)

( * ) Notice: Subject to any disclaimer, the term of this patent is extended or adjusted under 35 U.S.C. 154(b) by 52 days.

(21) Appl. No.: 13/353,595

(22) Filed: Jan. 19, 2012

(65) Prior Publication Data

US 2012/0114581 A1 May 10, 2012

Related U.S. Application Data

(62) Division of application No. 12/136,686, filed on Jun. 10, 2008, now abandoned.

(30) Foreign Application Priority Data

Jun. 18, 2007 (EP) .................................... 07110468

(51) Int. Cl.
| | | |
|---|---|---|
| *A61K 8/35* | (2006.01) | |
| *A61K 8/34* | (2006.01) | |
| *A61K 8/33* | (2006.01) | |
| *C11B 9/00* | (2006.01) | |

(52) U.S. Cl.
USPC ............. 514/724; 514/693; 514/675; 512/27; 512/25

(58) Field of Classification Search
CPC .................................. C11B 9/00; A61Q 13/00
See application file for complete search history.

(56) References Cited

U.S. PATENT DOCUMENTS

| | | | | |
|---|---|---|---|---|
| 4,137,180 | A | 1/1979 | Naik et al. ....................... 242/8.8 |
| 4,210,608 | A * | 7/1980 | Pinke ............................ 568/451 |
| 4,304,679 | A | 12/1981 | Hooper et al. ................. 252/106 |
| 5,236,615 | A | 8/1993 | Trinh et al. ............... 252/174.11 |
| 5,783,544 | A * | 7/1998 | Trinh et al. ................... 510/293 |
| 6,610,648 | B2 | 8/2003 | McGee et al. ................. 512/21 |
| 2002/0187168 | A1 | 12/2002 | Jensen et al. .................. 424/401 |
| 2003/0024997 | A1 | 2/2003 | Welch et al. .................... 239/53 |
| 2003/0068295 | A1 * | 4/2003 | Rohde et al. ................. 424/76.1 |
| 2004/0223871 | A1 | 11/2004 | Woo et al. ......................... 422/5 |
| 2005/0118223 | A1 | 6/2005 | Bernier et al. ................ 424/405 |

FOREIGN PATENT DOCUMENTS

| | | |
|---|---|---|
| EP | 0 174 821 A2 | 3/1986 |
| EP | 0 404 470 A1 | 12/1990 |
| EP | 0 799 885 A1 | 10/1997 |
| EP | 1 148 100 A2 | 10/2001 |
| JP | 07-018269 A | 1/1995 |
| JP | 2003-155488 A | 5/2003 |
| JP | 2005-160402 A | 6/2005 |
| WO | WO 97/26926 A1 | 7/1997 |
| WO | WO 97/34578 A1 | 9/1997 |
| WO | WO 97/34986 A1 | 9/1997 |
| WO | WO 02/49450 A2 | 6/2002 |
| WO | WO 03/070871 A1 | 8/2003 |

OTHER PUBLICATIONS

Buttery et al., "Fresh Tomato Volatiles, Composition and Sensory Studies," Flavor Chemistry: Trends and Developments, ACS Symposium Series, vol. 388, Chapter 17, pp. 213-222 (1989).
Covarrubias-Cervantes et al., "Saturated vapour pressure of aroma compounds at various temperatures," Food Chemistry, 85:221-229 (2004).
Hoffman, "Skunk Spray," Vet on Call, Rodale Press, Inc., Emmaus, PA, pp. 99-100 (1999).
International Search Report, Application No. PCT/IB2008/052147, dated Nov. 3, 2008.

* cited by examiner

*Primary Examiner* — Sue Liu
*Assistant Examiner* — Jessica Kassa
(74) *Attorney, Agent, or Firm* — Winston & Strawn LLP

(57) ABSTRACT

The present invention relates to the field of perfumery and more particularly to the field of malodor counteractancy. In particular, it relates to a method for application of malodor counteracting (MOC) compositions capable of neutralizing in an efficient manner, through chemical reactions, malodors of a large variety of origins and which can be encountered in the air, on textiles, bathroom or kitchen surfaces, and the like. The composition may be applied as is or in the form of a perfuming composition or in a consumer product or article containing the compound or perfume composition.

11 Claims, 3 Drawing Sheets

MALODOR COUNTERACTING COMPOSITIONS AND METHOD FOR THEIR USE

CROSS-REFERENCE TO RELATED APPLICATION

This application is a division of application Ser. No. 12/136,686 filed Jun. 10, 2008.

TECHNICAL FIELD

The present invention relates to the field of perfumery and more particularly to the field of malodor counteractancy. In particular, it relates to malodor counteracting (MOC) compositions capable of neutralizing in an efficient manner, through chemical reactions, malodors of a large variety of origins and which can be encountered in the air, on textiles, bathroom or kitchen surfaces, and the like.

BACKGROUND OF THE INVENTION

The prior art richness in reports of methods and compositions to counteract and/or mask malodors is such that a complete review of all the methods and compositions prior reported in this context is impossible here. It is clear however that there still exists a need to continue searching alternative ways of solving the malodor problem, as evidenced by the constant publications in this field.

Some prior publications relate to the use of aldehydes, ketones and/or alcohols in deodorizing compositions in order to neutralize malodors. Among these documents, there can be cited as particularly pertinent the following ones.

U.S. Pat. No. 4,304,679 discloses a deodorant detergent product comprising a deodorant composition intended to counter the human body malodor. The disclosed composition must comprise at least four compounds from different classes and may comprise a mixture of aldehydes, ketones and alcohols. These three classes of compounds are described in a very general manner and there are no example comprising mixtures of alcohols, aldehydes and ketones such as presently claimed.

U.S. Pat. No. 6,610,648 describes fragrance compositions containing one or more malodor counteractancy compounds, and mainly ester derivatives. The composition may be used, in combination with fragrance ingredients to reduce the perception of malodors. The fragrance ingredients may be selected from a wide range of different compound types, including alcohols, aldehydes and ketones in general. The described compositions are used either for dispersing into space or for imparting a malodor counteracting effect to a substrate. There is no description of compositions such as presently disclosed.

The publication US 2004/0223871 discloses an air freshener and methods for freshening air, which may contain a perfume composition in conjunction with a malodor counteractant. Malodor neutralization via vapor phase technology, meaning the use of malodor counteractants that mitigate malodor in the air via chemical reactions or neutralization, is described. The disclosed air freshening composition may comprise one or more enones and one or more aliphatic, linear and/or branched aldehydes with no more than two double bonds, comprising 7 to 22 carbon atoms. Furthermore, the use of LILIAL® (tradename of Givaudan SA, Switzerland), which is an aldehyde comprising an aromatic moiety, to neutralize butylamine is described to exemplify the neutralization of amines by aldehydes through chemical reaction. Again, the specific compositions of the invention are not disclosed.

EP 0404470 discloses compositions of fragrance materials, which can confer deodorant effects in detergent products. A wide range of perfumery materials may be incorporated in such compositions and, in particular, such compositions may comprise aldehydes, ketones and/or alcohols. These classes of compounds are described in a very general way and no specific example of mixtures of aldehydes, ketones and alcohols according to the invention is given in that patent.

WO 03/070871 discloses a malodor counteracting and/or masking composition that is particularly effective against malodor developed during soaking and/or hand washing laundry. These compositions may comprise aliphatic aldehydes comprising 1 to 12 carbon atoms. Nevertheless the use of mixtures of such aldehydes with aliphatic ketones and primary alcohols as MOC compositions is not disclosed.

SUMMARY OF THE INVENTION

The present invention now relates to a malodor counteracting composition consisting of specific malodor counteracting (MOC) mixtures of fragrance ingredients. More particularly, the new MOC ingredients of the invention contain at least one aliphatic aldehyde, at least one aliphatic ketone and at least one primary alcohol.

The invention also relates to methods of use of the MOC compositions to counteract malodor as well as to perfuming compositions and finished consumer articles or products containing them, such as air fresheners, kitchen or toilet/bathroom cleaning or freshening products, textile treatment products and products for application on the human skin or hair, or on animal fur and skin, litter containers and animal cages.

DETAILED DESCRIPTION OF THE PREFERRED EMBODIMENTS

Figure 1:
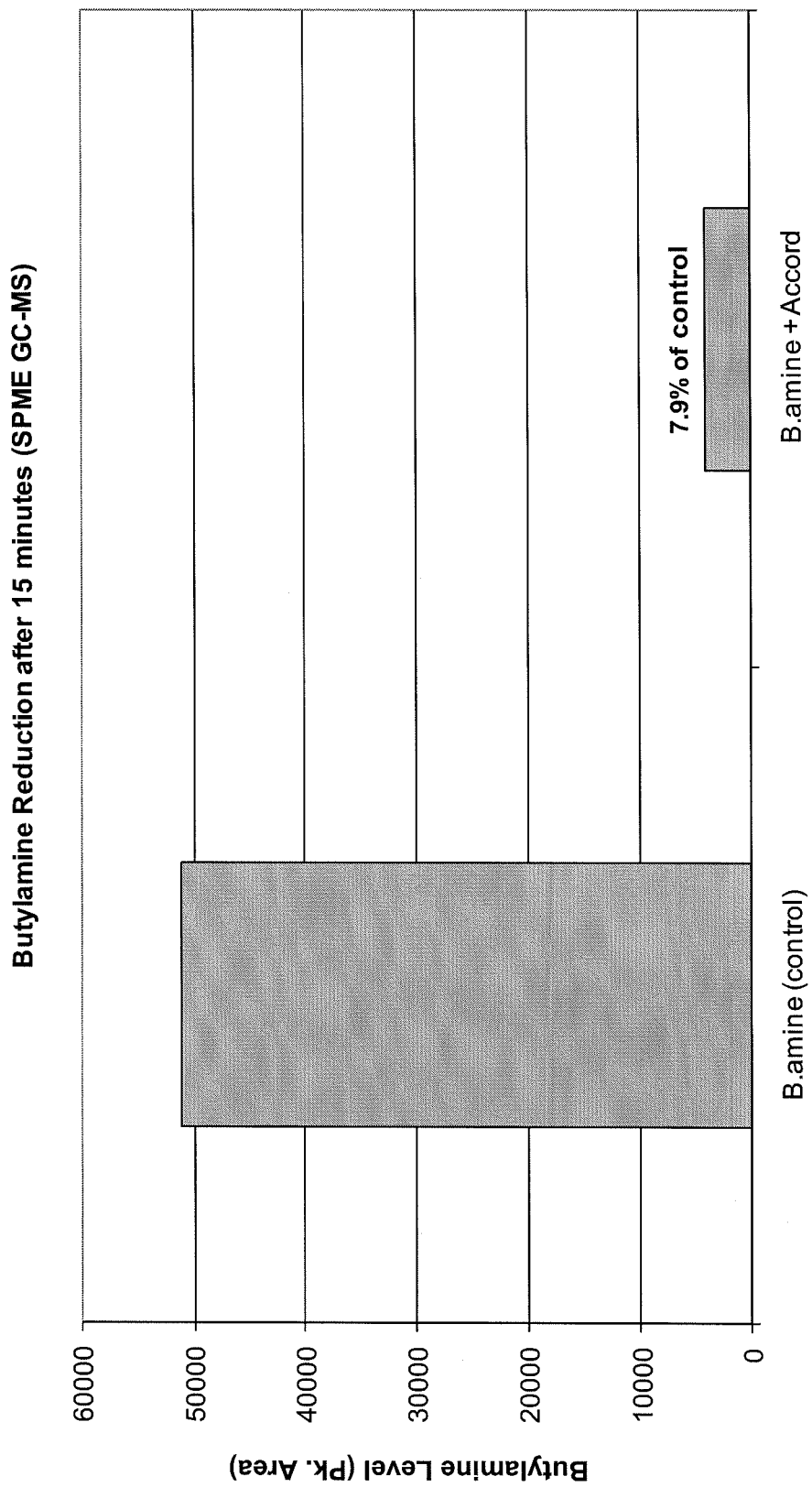
FIG. 1 shows the butylamine level (peak area) measured by GC-MS for the samples of Example 1, part B, respectively containing butylamine alone and butylamine with the MOC composition described in part A of the same example. This figure shows a significant neutralization of butylamine, a compound with a typical amine, fishy malodor, by the MOC composition of the invention.

We have now surprisingly established that mixtures of the compounds of groups (I), (II) and (III) described below possess very useful malodor counteracting (MOC) properties and that they are capable of masking and/or neutralizing a large variety of malodors of importance, either developed in the human or animal bodies or generated as a result of human or animal general activities. The mixtures of the invention, as malodor counteracting (MOC) compositions, can be advantageously used in the design and conception of fragrance compositions and consumer products intended for efficient prevention and/or masking of such malodors.

As "malodor counteracting (MOC) compositions" we mean here a mixture of compounds of Groups (I), (II) and (III) as defined below and which is capable of reducing the perception of malodor, i.e. of an odor that is unpleasant or offensive to the human nose. These compounds (later on referred to as "MOC compounds" or "materials") have the ability to react with key compounds causing known malodors. The reactions result in reduction of the malodor materials' airborne levels and consequent reduction in the perception of the malodor.

According to the invention, the MOC compositions are shown to reduce the malodor perceived from compositions formed either according to International standards or as indicated in the examples further on, and which are representative of the various odors of interest generally recognized as being unpleasant or offensive to the human nose.

The present invention relates to MOC compositions comprising at least one ingredient selected from Group (I) compounds, at least one ingredient selected from Group (II) compounds and at least one ingredient selected from the Group (III) compounds. Group (I), Group (II) and Group (III) compounds are defined as follows:
a) Group (I): aldehydes of formula $R^1CHO$, wherein $R^1$ is an aliphatic linear or branched, saturated or unsaturated carbon chain containing from 1 to 12 carbon atoms;
b) Group (II): ketones of formula $R^2COR^3$, wherein $R^2$ is an ethyl or methyl group and $R^3$ is an aliphatic linear or branched, saturated or unsaturated carbon chain containing from 1 to 12 carbon atoms; and
c) Group (III): primary alcohols of formula $R^4CH_2OH$, wherein $R^4$ is an aliphatic linear or branched, saturated or unsaturated carbon chain containing 1 to 12 carbon atoms, optionally substituted with an aromatic moiety.

According to a preferred embodiment, the MOC composition of the invention consists of a mixture of at least one ingredient selected from Group (I) compounds, at least one ingredient selected form Group (II) compounds and at least one ingredient selected from Group (III) compounds.

According to another preferred embodiment, the aldehyde of Group (I) is hexanal, decanal, octanal, nonanal, 9-undecenal, (+−)-2,6-dimethyl-5-heptenal or (Z)-4-dodecenal. According to a more preferred embodiment, the aldehyde of Group (I) is hexanal.

According to another preferred embodiment, the ketone of Group (II) is 2-octanone or 2-heptanone, and more preferably 2-octanone.

Suitable primary alcohols of Group (III) include decan-1-ol, hexan-1-ol, octan-1-ol, (Z)-3-hexen-1-ol or benzylalcohol. According to a more preferred embodiment, the primary alcohol of Group (III) is hexan-1-ol.

MOC compositions comprising a mixture of hexanal, 2-octanone and hexan-1-ol are particularly effective.

According to another preferred embodiment, the MOC composition of the invention comprises, as aldehydes of Group (I), compounds selected from at least two, preferably from at least three, preferably from at least four, preferably from at least five, preferably form all of the following sub-groups:
Sub-group a): aldehydes consisting of a linear, saturated or unsaturated, aliphatic $C_7$ chain, optionally substituted with up to six carbon atoms;
Sub-group b): aldehydes consisting of a linear, saturated or unsaturated, aliphatic $C_8$ chain, optionally substituted with up to five carbon atoms;
Sub-group c): aldehydes consisting of a linear, saturated or unsaturated, aliphatic $C_9$ chain, optionally substituted with up to four carbon atoms;
Sub-group d): aldehydes consisting of a linear, saturated or unsaturated, aliphatic $C_{10}$ chain, optionally substituted with up to three carbon atoms;
Sub-group e): aldehydes consisting of a linear, saturated or unsaturated, aliphatic $C_{11}$ chain, optionally substituted with up to two carbon atoms; or
Sub-group f): aldehydes consisting of a linear, saturated or unsaturated, aliphatic $C_{12}$ chain, optionally substituted with one carbon atom.

According to a further preferred embodiment, the MOC composition of the invention comprises, as alcohols of Group (III), compounds selected from at least two, preferably from all of the following sub-groups:
Sub-group g): alcohols consisting of a linear, saturated or unsaturated, aliphatic $C_6$ chain, optionally substituted with up to seven carbon atoms;
Sub-group h): alcohols consisting of a linear, saturated or unsaturated, aliphatic $C_8$ chain, optionally substituted with up to five carbon atoms; or
Sub-group i): alcohols consisting of a linear, saturated or unsaturated, aliphatic $C_{10}$ chain, optionally substituted with up to three carbon atoms.

According to a more preferred embodiment, the MOC composition comprises, as aldehydes of Group (I), compounds selected from at least two, preferably from at least three, preferably from at least four, preferably from at least five, preferably from all of sub-groups a) to f), as defined above and, as alcohols of Group (III), compounds selected from at least two, preferably from all of sub-groups g) to i), as defined above.

According to a more preferred embodiment, the MOC composition comprises as aldehydes of Group (I), at least two, preferably at least three, preferably at least four, preferably at least five, preferably all compounds from the group consisting of 2,6-dimethyl-5-heptenal, octanal, nonanal, decanal, 9-undecenal and (Z)-4-dodecenal and/or, as alcohols of Group (III), at least two, preferably at least three, preferably all compounds from the group consisting of hexanol, (Z)-3-hexen-1-ol, octanol and decanol.

According to an even more preferred embodiment, the MOC composition of the invention comprises a mixture of decanal and octanal and/or a mixture of nonanal and 9-undecenal.

According to another preferred embodiment of the invention, the MOC composition comprises at least one, preferably at least two, preferably all compounds from the group consisting of IRALIA® Total (mixture of 8-methyl-alpha-ionone and 10-methyl-alpha-ionone, origin: Firmenich SA, Geneva, Switzerland), HIVERNAL® (a mixture of 3-(3,3-dimethyl-5-indanyl)propanal and 3-(1,1-dimethyl-5-indanyl)propanal, origin: Firmenich SA, Geneva, Switzerland) and PERYCOROLLE® ((S)-1,8-p-menthadiene-7-ol, origin: Firmenich SA, Geneva, Switzerland).

According to a further embodiment of the invention, the compounds of groups (I), (II) and (III) are characterized by a vapor pressure above 0.03 mmHg, as calculated in Pa using the software EPIwin v. 3.10 (2000, available at the US Environmental Protection Agency) and then converted to mmHg.

The amount of compound or compounds of Group (I), of compound or compounds of Group (II) and of compound or compounds of Group (III) in the MOC composition of the invention can vary in a wide range of values comprised between 1 and 98% by weight of each of the three components, relative to the total weight of the MOC composition.

For each combination, the optimum relative concentrations can easily be established by the person skilled in the art, on the basis of his general knowledge with the help of the examples presented further on, the suitable concentrations being dependent on the desired effect of the composition. According to a preferred embodiment, the MOC composition comprises between 55 and 60% by weight of compound or compounds of Group (I), between 20 and 25% by weight of compound or compounds of Group (II) and between 20 and 25% by weight of compound or compounds of Group (III), these concentrations being relative to the total weight of the MOC composition.

These MOC compositions are useful against a wide variety of different malodors, for example lower aliphatic carboxylic acids with a carbon chain containing up to 8 carbon atoms, which are key components of the rancid, sweaty and bathroom malodor, lower aliphatic amines which are key components of fishy, urinous and sweaty malodor or lower aliphatic thiols, which are key components of bathroom, cooking, depilatory and garbage malodors. A combination of Group (I), Group (II) and Group (III) compounds is able to act against the most common malodors and can be advantageously used in varied situations where it is desired to suppress malodors of different origins.

The MOC compositions of the invention can either be used to neutralize malodor in the air or on a surface. A MOC composition according to any of the above embodiments can be used at 100% as a powerful malodor counteractant, or in admixture together with other ingredients.

The invention also provides perfuming compositions comprising:
i) a MOC composition according to any of the embodiments exposed above;
ii) at least one ingredient selected from the group consisting of a perfumery base and a perfumery carrier; and
iii) optionally at least one perfumery adjuvant.

The MOC composition will typically constitute from 0.05 to 50% by weight, and more preferably from 0.05 to 10% by weight, relative to the total weight of the perfuming composition according to the invention.

Generally speaking, by "perfumery base" we mean here a composition comprising at least one perfuming co-ingredient, which is typically not a compound of Group (I), (II) or (III).

By perfuming "co-ingredient" it is meant here a compound that is used in a perfuming preparation or composition to impart a hedonic effect. In other words such a co-ingredient, to be considered as being a perfuming one, must be recognized by a person skilled in the art as being able to impart or modify, in a positive or pleasant way, the odor of a composition, and not just as having an odor.

The nature and type of the perfuming co-ingredients present in the base do not warrant a more detailed description here, which in any case would not be exhaustive, the skilled person being able to select them on the basis of its general knowledge and according to the intended use or application and the desired organoleptic effect. In general terms, these perfuming co-ingredients belong to chemical classes as varied as alcohols, aldehydes, ketones, esters, ethers, acetates, nitriles, terpene hydrocarbons, nitrogenous or sulphurous heterocyclic compounds and essential oils, and the perfuming co-ingredients can be of natural or synthetic origin. Many of these co-ingredients are in any case listed in reference texts such as the book by S. Arctander, Perfume and Flavor Chemicals, 1969, Montclair, N.J., USA, or its more recent versions, or in other works of a similar nature, as well as in the abundant patent literature in the field of perfumery. It is also understood that the co-ingredients may also be compounds known to release in a controlled manner various types of perfuming compounds.

By "perfumery carrier" we mean here a material which is practically neutral from a perfumery point of view, i.e. that does not significantly alter the organoleptic properties of perfuming ingredients. This carrier may be a liquid or a solid.

As liquid carrier one may cite, as non-limiting examples, an emulsifying system, i.e. a solvent and a surfactant system, or a solvent commonly used in perfumery. A detailed description of the nature and type of solvents commonly used in perfumery cannot be exhaustive. However, one can cite as non-limiting examples solvents such as dipropylene glycol, diethyl phthalate, isopropyl myristate, benzyl benzoate, 2-(2-ethoxyethoxy)-1-ethanol or ethyl citrate, which are the most commonly used.

The perfuming co-ingredients may also be present in a solid form, encapsulated or dispersed in solid carriers. As appropriate solid carriers one may cite, as non-limiting examples, absorbing gums or polymers, or yet encapsulating materials. Examples of such materials may comprise wall-forming and plasticizing materials, such as mono, di- or tri-saccharides, natural or modified starches, hydrocolloids, cellulose derivatives, polyvinyl acetates, polyvinylalcohols, proteins or pectins, or yet the materials cited in reference texts such as H. Scherz, Hydrokolloids: Stabilisatoren, Dickungs- und Gehermittel in Lebensmittel, Band 2 der Schriftenreihe Lebensmittelchemie, Lebensmittelqualität, Behr's Verlag-GmbH & Co., Hamburg, 1996. The encapsulation is a well-known process to a person skilled in the art, and may be performed, for instance, using techniques such as spray-drying, agglomeration or yet extrusion; or consists of a coating encapsulation method, including coacervation and complex coacervation techniques.

Generally speaking, by "perfumery adjuvant" we mean here an ingredient capable of imparting additional added benefit such as a color, a particular light resistance, chemical stability and etc. A detailed description of the nature and type of adjuvant commonly used in perfuming compositions cannot be exhaustive, but it has to be mentioned that the ingredients are well known to a person skilled in the art.

The invention also provides a consumer article or product comprising:
i) a MOC composition or a perfuming composition according to any of the above-exposed embodiments; and
ii) a consumer product base.

The invention's MOC compositions, on their own or as components of the perfuming compositions according to the invention, can be advantageously used in all the fields or modern perfumery to positively impart or modify the odor of a product into which they are incorporated. As non-limiting examples, such article or product may be a perfume, a cologne, an after-shave lotion, a perfumed soap, a shower or bath salt, mousse, oil or gel, a hygiene product, a body care product, a hair care product such as a shampoo, a deodorant or antiperspirant, a cosmetic preparation, an air freshener, a solid or liquid detergent, a fabric softener or refresher, a bleach, an ironing water, a paper or non-woven substrate, a wipe or a bleach. Preferred consumer articles or products are deodorant or antiperspirants, air fresheners and fabric softeners or refreshers.

For the sake of clarity, by "consumer product base" we mean here a base, which is distinct from, but compatible with, the MOC and/or perfuming compositions of the invention, and which is typically formed of substances capable of achieving the functional effect typically required from that product such as cleaning, softening, freshening, deodorizing and others. Typical consumer product bases are the functional mixtures of ingredients that form the base of for example a surface or textile detergent or soap, a surface or textile softener, an air freshener, a cosmetic preparation, a deodorant, etc.

The nature and type of the constituents of the consumer product base do not warrant a more detailed description here, which in any case would not be exhaustive, the skilled person being able to select them on the basis of its general knowledge and according to the nature and the desired effect of the product.

Some consumer product bases may represent an aggressive medium for the MOC or perfuming compositions of the invention, so that it may be necessary to protect the latter from premature decomposition, for example by encapsulation.

The MOC and perfuming compositions intended for air freshener use may comprise some optional ingredients acting as, for example, solvents, thickeners, anti-oxidants, dyes, bittering agents and UV inhibitors.

The presence of one or more solvents may be useful to have a single-phase liquid and/or to modulate the speed of evaporation of the active material into the surrounding air. These solvents may belong to the families of isoparaffins, paraffins, hydrocarbons, namely glycols, glycol ethers, glycol ether esters, esters or ketones.

Examples of commercially available solvents useful to the invention are known under the tradename ISOPAR® H, J, K, L, M, P or V (isoparaffins; origin: Exxon Chemical), NOR-PAR® 12 or 15 (paraffins; origin: Exxon Chemical), EXXSOL® D 155/170, D 40, D 180/200, D 220/230, D 60, D 70, D 80, D 100, D 110 or D 120 (dearomatised Hydrocarbons; origin: Exxon Chemical), DOWANOL® PM, DPM, TPM, PnB, DPnB, TPnB, PnP or DPnP (glycol ethers; origin: Dow Chemical Company), EASTMAN® EP, EB, EEH, DM, DE, DP or DB (glycol ethers; origin: Eastman Chemical Company), DOWANOL® PMA or PGDA (glycol ether esters; origin: Dow Chemical Company) or EASTMAN® EB acetate, EASTMAN® DE acetate, EASTMAN® DB acetate, EASTMAN® EEP (all glycol ether esters; all origin: Eastman Chemical Company).

Other examples of solvents useful are di-propylene glycol, propylene glycol, ethylene glycol ethyl ether acetate, ethylene glycol diacetate, isopropyl myristate, diethyl phthalate, 2-ethylhexyl acetate, methyl n-amyl ketone or di-isobutyl ketone.

Suitable dyes are oil-soluble and can be found in the Colour Index International, published by The Society of Dyers and Colourist. Non-limiting examples of suitable dyes are derivatives of the anthraquinone, methine, azo, triarylmethane, triphenylmethane, azine, aminoketone, spirooxazine, thioxanthene, phthalocyanine, perylene, benzopyran or perinone families. Examples of such dyes which are commercially available are known under the tradename SANDOPLAST® Violet RSB, Violet FBL, Green GSB, Blue 2B or SAVINYL® Blue RS (all anthraquinone derivatives; origin: Clariant Huningue S.A.), OILSOL® Blue DB (anthraquinone; origin: Morton International Ltd.), SANDOPLAST® Yellow 3G (methine; origin: Clariant Huningue S.A.), SAVINYL® Scarlet RLS (azo metal complex; origin: Clariant Huningue S.A.), OILSOL® Yellow SEG (monoazo; origin: Morton International Ltd.), FAT ORANGE® R (monoazo; origin: Hoechst AG), FAT RED® 5B (diazo; origin: Hoechst AG), NEOZAPON® Blue 807 (phtalocyanine; origin: BASF AG), FLUOROL® Green Golden (perylene; origin: BASF AG).

Typical examples of fabric detergents or softener compositions into which the perfuming or MOC compositions of the invention can be incorporated are described in WO 97/34986 or in U.S. Pat. Nos. 4,137,180 and 5,236,615 or EP 799 885. Other typical detergent and softening compositions which can be used are described in works such as Ullman's Encyclopedia of Industrial Chemistry, vol. A8, pages 315-448 (1987) and vol. A25, pages 747-817 (1994); Flick, Advanced Cleaning Product Formulations, Noye Publication, Park Ridge, N.J. (1989); Showell, in Surfactant Science Series, vol. 71: Powdered Detergents, Marcel Dekker, New York (1988); Proceedings of the World Conference on Detergents (4th, 1998, Montreux, Switzerland), AOCS print.

The proportions in which the MOC compositions, or the perfuming compositions containing them, can be incorporated into the various aforementioned consumer articles or products may vary within a wide range of values. In many of these consumer products, the amount of perfuming composition according to the invention that is added to the consumer product is similar to the typical perfume amount that can be found currently in each type of consumer product. This amount can be easily adjusted by the skilled formulator according to the perfuming and malodor counteracting effect that is desired to achieve and the nature of the consumer product.

Some indicative concentrations are given here as non-limiting examples.

In the case of an air freshener for instance, the MOC or perfuming composition intended for diffusion into its surroundings is usually contained in a recipient forming the main body of the air freshener. The composition may be entirely formed of the perfuming or MOC composition of the invention. Alternatively it may be together with an appropriate solvent such as water and or an organic solvent.

Generally speaking, an air freshener may comprise between 0.1 and 100% by weight of the MOC or perfuming composition according to the invention, relative to the total weight of the consumer article or product. The appropriate concentrations differ according to the type of air freshener. In an air freshener that can be sprayed, a concentration of 0.1 to 5% can be used, whereas electrical and/or wick type air fresheners can have up to 100% MOC or perfuming composition, and more typically between 50 and 100%.

In other types of consumer articles or products, for example detergents, deodorants, antiperspirants and all other suitable perfumed product, the concentration may usually be comprised between 0.1 and 20%, preferably between 0.5 and 10% and more preferably between 1 and 5%.

The invention also provides a method to counteract malodors of the above-mentioned types. The method comprises applying to spaces or surfaces intended to be deodorized or freshened, a MOC composition, a perfuming composition or a consumer product or article according to the invention, in an amount sufficient to reduce, mask, eliminate or prevent any malodor perception from the spaces or surfaces. In particular, the spaces are closed spaces such as rooms and cupboards. As examples of surfaces, the odor of which can thus be improved, one can cite human skin or hair, animal skin or fur, kitchen or toilet surfaces, the surface of animal cages or litter containers, rubbish containers surfaces, textile and laundry surfaces, glass windows, dishes and crockery surfaces, etc. In a particular embodiment of the invention, the method comprises using a body deodorant or antiperspirant, an air freshener or a fabric softener or refresher.

In fact the MOC composition of the invention is used to counteract the malodor by reaction of the ingredients of the composition with compounds responsible of the malodor in the gaseous phase.

EXAMPLES

The following examples are further illustrative of the present invention embodiments, and further demonstrate the advantages of the invention devices relative to prior art teachings.

Example 1

A. Preparation of a MOC Composition According to the Invention

A MOC composition according to the invention was prepared by admixing the following ingredients:

| Ingredients | Quantity |
|---|---|
| Decanol | 6.00 |
| Hexanol | 2.00 |
| Octanol | 4.00 |
| Decanal | 15.00 |
| Octanal | 7.50 |
| Nonanal | 4.00 |
| 9-undecenal | 2.00 |
| (−)-(R)-1(6),8-p-menthadien-2-one | 10.00 |
| (+−)-2,6-dimethyl-5-heptenal | 5.00 |
| 2-octanone | 4.00 |
| (Z)-3-hexen-1-ol | 10.00 |
| (Z)-4-dodecenal | 0.50 |
| 3-phenylbutanal | 10.00 |
| TOTAL | 80.00 |

B. Effectiveness of the Composition

Use of Solid Phase Microextraction (SPME) to Demonstrate Malodor Material Reduction in the Presence of the Above-Described MOC Composition First of all, a 20% solution of butylamine in EtOH was prepared. 0.005 ml of this solution were transferred with a pipette onto a watch glass at the bottom of two 3 L desiccators. 3 g of the MOC composition prepared in part A were placed on a cellulose pad in a Petri-dish, which was placed in one of the desiccator, on a tray above the watch glass containing the butylamine solution. The desiccator was then covered with the lid. No MOC composition was added to the other desiccator, used as a control containing only butylamine. After 15 min, a SPME fiber was placed in the headspace of each desiccator and the fiber was allowed to absorb for 5 minutes. Finally, the fiber was desorbed and analyzed via GC-MS.

The graph of FIG. 1 represents the different peak areas of butylamine (butylamine level) as measured by GC-MS at 15 minutes in the control test containing only butylamine (on the left) and in the sample containing butylamine together with the MOC composition (on the right). This graph shows the high efficiency of the MOC composition of the invention in counteracting the malodor of butylamine, which is a key component of several malodors.

Example 2

A. Preparation of a MOC Composition According to the Invention

A MOC composition according to the invention was prepared by admixing the following ingredients:

| Ingredients | Quantity |
|---|---|
| Decanol | 6.00 |
| Hexanol | 2.00 |
| Octanol | 4.00 |
| Decanal | 20.00 |
| Octanal | 10.00 |
| Nonanal | 5.00 |
| 9-undecenal | 7.50 |
| (+−)-(E)-1-(2,6,6-trimethyl-2-cyclohexen-1-yl)-2-buten-1-one | 5.00 |
| IRALIA ® Total [1] | 10.00 |
| (+−)-2,6-dimethyl-5-heptenal | 5.00 |
| 2-octanone | 5.00 |
| (Z)-3-hexen-1-ol | 10.00 |
| (Z)-4-dodecenal | 0.50 |
| 3-phenylbutanal | 10.00 |
| TOTAL | 100.00 |

[1] Mixture of 8-methyl-alpha-ionone and 10-methyl-alpha-ionone, origin: Firmenich SA, Geneva, Switzerland)

B. Sensory Analysis

Efficiency of the MOC Composition on the Reduction of a Synthetic Kitchen Malodor A typical synthetic kitchen malodor* is prepared by admixing the following ingredients:

| Ingredient | % w/w |
|---|---|
| Diacetyl | 3.85 |
| Pyridine | 3.85 |
| Allyl sulfide | 9.23 |
| Methyl sulfide | 40.00 |
| Heptaldehyde | 3.85 |
| Paraldehyde | 1.90 |
| Propionic acid | 36.92 |
| Acetic acid, glacial | 0.40 |
| TOTAL | 100.00 |

* U.S. General Services Administration Federal Supply Service Interim Specification, FA 200-3

The ability of a membrane air freshener comprising a fragrance alone or a fragrance together with a MOC composition as described in part A of this example (in an amount of 4% by weight relative to the total weight of the mixture), to neutralize the synthetic kitchen malodor, was tested by sensory evaluation using a panel of trained panelists.

By "trained panelists" we mean here individuals that had previously been screened for olfactive acuity and were experienced comparing odorant samples. Moreover, the panelists were prior acquainted with the malodor sample before carrying out the evaluation of the samples counteracting effect.

Six fragrance samples were prepared. Three of them contained one of the fragrance materials alone (Fragrance 1, 2 or 3) and the other three contained one of these fragrance materials together with the MOC composition disclosed in part A.

Two different malodor samples were prepared. One sample contained a cellulose pad with a level of malodor deemed to be "just perceptible". This sample, intended to be used as a control, was named the 10% sample (see FIG. 2). The other sample contained a cellulose pad with ten times the malodor concentration of the 10% control sample. This second sample, which showed an unacceptable malodor level, was designated as the 100% sample (see FIG. 2).

Each of the six fragrance samples was placed in a 200 L drum for 1 hour. Then, the 100% malodor sample was added to each drum. The 10% malodor sample was placed in another 200 L drum without any fragrance sample, to serve as the control sample. Evaluations took place 10 minutes later.

Using a paired comparison method, on blind test, at least 20 panelists were asked to choose, between a drum containing the 10% malodor sample and one containing the 100% malodor sample together with the fragrance sample, which one had the least malodor. The test was considered as passed if a statistically significant number of panelists chose the drum containing the 100% sample as the one having the least malodor.

Figure 2:
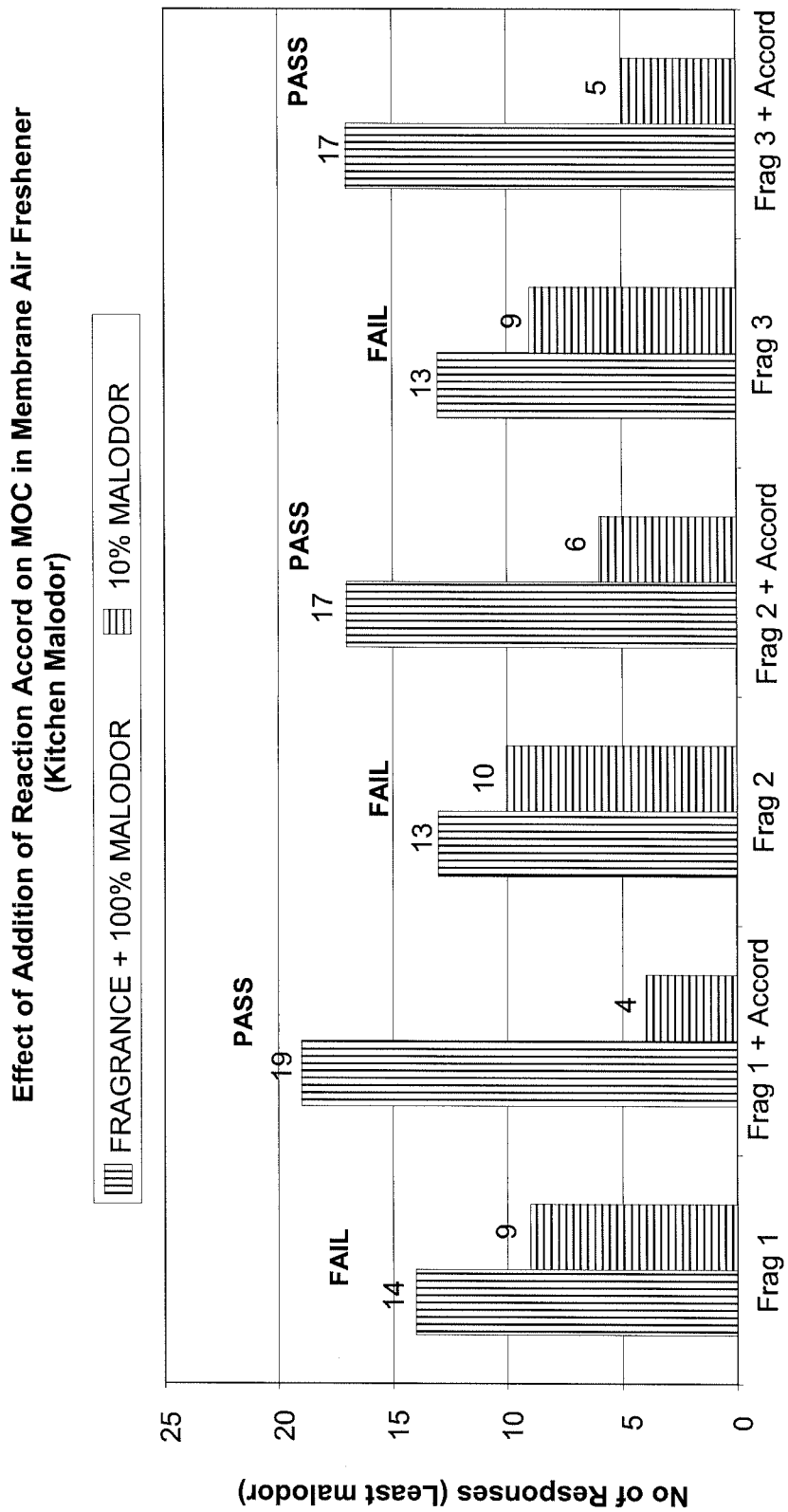
FIG. 2 is a graph summarizing the results of the sensory tests of Example 2, part B. This graph shows that the reduction of kitchen malodor is only significant when the fragrance is admixed with the MOC composition of the invention as described in Example 2, part A.

FIG. 2 shows the results of these sensory tests. For each comparison, the darker columns represent the number of panelists who chose the 100% malodor with the MOC composition and the lighter columns represent the number of panelists who chose the 10% malodor.

As is apparent from this figure, the fragrances alone failed to reduce significantly the kitchen malodor, whereas a significant neutralization of that odor could be observed when the fragrance was combined with the above-described MOC composition.

C. Sensory Analysis

Efficiency of the MOC Composition on the Reduction of a Synthetic Bathroom Malodor A typical synthetic bathroom malodor* is prepared by admixing the following ingredients:

| Ingredient | % w/w |
|---|---|
| Dipropylene glycol | 62.82 |
| Thioglycolic acid | 21.18 |
| n-Caproic acid | 6.00 |
| n-Methylmorpholine | 6.00 |
| 4-Methylphenyl 3-Methylbutanoate | 2.18 |
| Skatole | 0.91 |
| 2-Naphthalenethiol | 0.91 |
| TOTAL | 100.00 |

* U.S. General Services Administration Federal Supply Service Interim Specification, FA 200-3

The ability of an aerosol air freshener comprising either a fragrance alone or a fragrance together with a MOC composition as described in part A of this example, to neutralize the synthetic bathroom malodor, was tested by sensory evaluation using a panel of trained panelists. The fragrance or the fragrance together with the MOC composition was present in an amount of 0.5% by weight relative to the total content of the aerosol, whereas the MOC composition was present in an amount of 2% by weight relative to the total weight of the fragrance.

The "trained panelists" are defined in the same way as for part B of the present example.

Two fragrance samples were prepared. One of them contained a fragrance material alone (SWEET SPRING 164152, origin: Firmenich SA) and the other one contained the same fragrance material together with the MOC composition disclosed in part A (SWEET SPRING WJK 9438-14B, origin: Firmenich SA).

Two different malodor samples were prepared as in part B of this example. One sample contained a cellulose pad with a level of malodor deemed to be "just perceptible". This sample, intended to be used as a control, was named the 10% sample (see FIG. 3). The other sample contained a cellulose pad with ten times the malodor concentration of the 10% control sample. This second sample, which showed an odor level unacceptable as compared to the usual bathroom malodors in the home, was designated as the 100% sample (see FIG. 3). Each of these samples was prepared in the form of an aerosol in a manner known in itself.

The malodor samples were placed in 2.5 $M^3$ cabins for 10 minutes. Then, each of the fragrance samples was sprayed for two seconds into a cabin containing the 100% malodor sample. No fragrance sample was sprayed in the cabin containing the 10% malodor sample used as a control. The evaluation took place immediately after.

Using a paired comparison method, on a blind test, at least 20 panelists were asked to choose, between the cabin containing the 10% malodor sample and the one containing the 100% malodor sample together with the fragrance sample, which one had the least malodor. The test was considered as passed if a statistically significant number of panelists chose the cabin containing the 100% sample as the one having the least malodor.

Figure 3:
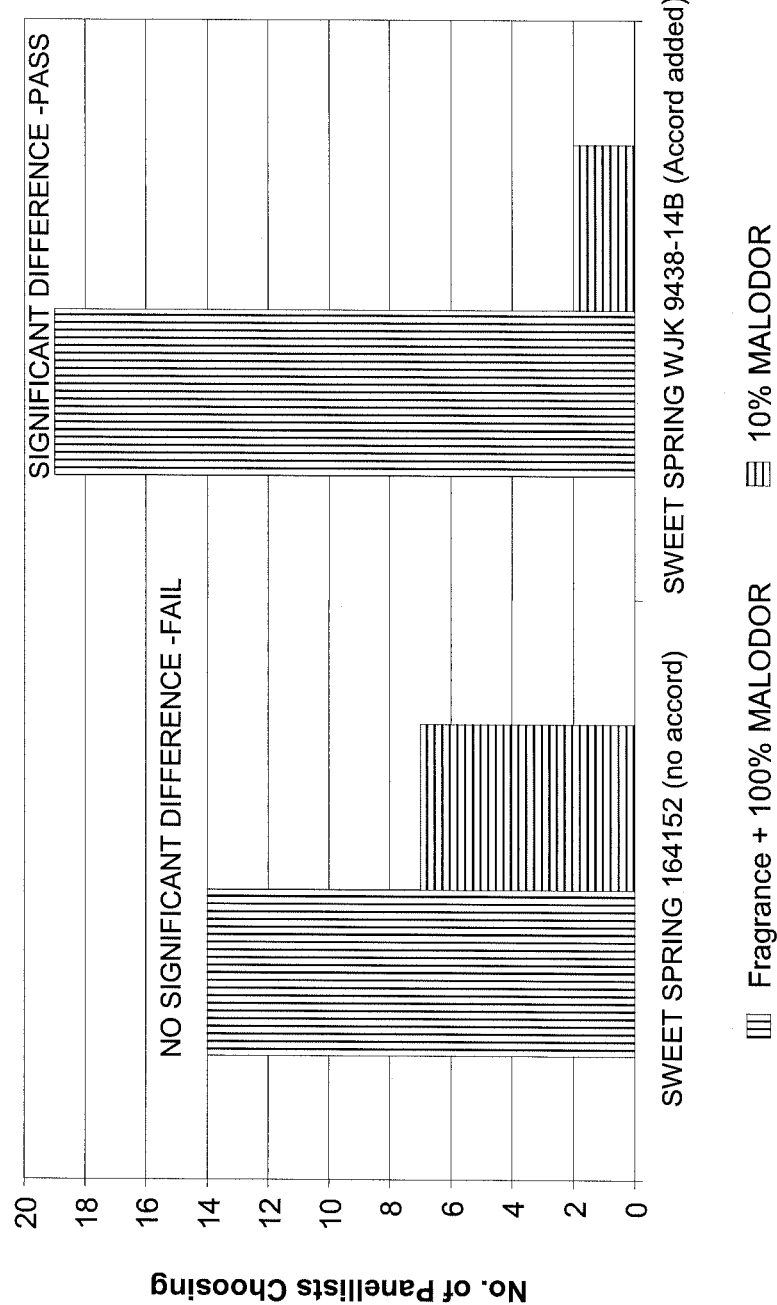
FIG. 3 is a graph summarizing the results of the sensory tests of Example 2, part C. This graph shows that the reduction of bathroom malodor is only significant when the fragrance is admixed with the MOC composition of the invention as described in Example 2, part A.

FIG. 3 shows the results of these sensory tests. For each comparison, the light columns represent the number of panelists who chose the 100% malodor with the MOC composition and the darker columns represent the number of panelists who chose the 10% malodor alone as the least malodor.

As is apparent from this figure, the fragrance material alone failed to reduce significantly the bathroom malodor, whereas a significant neutralization of that odor could be observed when the fragrance was combined with the above-described MOC composition.

Example 3

A MOC composition according to the invention was prepared by admixing the following ingredients:

| Ingredients | Quantity |
|---|---|
| Undecanal | 300 |
| Nonanal | 200 |
| 9-Undecenal | 100 |
| Citronellol | 2000 |
| HIVERNAL ® [1] | 100 |
| IRALIA ® [2] Total | 1000 |
| Methylhexylketone | 300 |
| PERYCOROLLE ® [3] | 1000 |
| Phenethylol | 4000 |
| (Z)-3-Hexen-1-ol | 1000 |
| TOTAL | 10000 |

[1] Mixture of 3-(3,3-dimethyl-5-indanyl)propanal and 3-(1,1-dimethyl-5-indanyl)propanal (origin: Firmenich SA, Geneva, Switzerland);
[2] Mixture of 8-methyl-alpha-ionone and 10-methyl-alpha-ionone (origin: Firmenich SA, Geneva, Switzerland);
[3] (S)-1,8-p-menthadiene-7-ol (origin: Firmenich SA, Geneva, Switzerland).

Example 4

A MOC composition according to the invention was prepared by admixing the following ingredients:

| Ingredients | Quantity |
|---|---|
| Decanol | 500 |
| Octanol | 300 |
| Decanal | 750 |
| Octanal | 250 |
| Citral | 2500 |
| Citronellal | 750 |
| Decenal [1] | 20 |
| Geraniol | 2000 |

-continued

| Ingredients | Quantity |
|---|---|
| LIMINAL ® [2] | 300 |
| Methylheptenone | 500 |
| Methylpentylketone | 100 |
| 4-(2,2,3,6-Tetramethyl-1-cyclohexyl)-3-buten-2-one [3] | 500 |
| (E)-2-Hexen-1-ol | 1500 |
| Tangerinal [4] | 30 |
| TOTAL | 10000 |

[1] Mixture of isomers 8- and 9- (origin: Firmenich SA, Geneva, Switzerland);
[2] (4R)-1-p-menthene-9-carbaldehyde (origin: Firmenich SA, Geneva, Switzerland);
[3] Origin: Firmenich SA, Geneva, Switzerland;
[4] (Z)-4-dodecenal (origin: Firmenich SA, Geneva, Switzerland)

What is claimed is:

1. A method to counteract malodors, which comprises applying to a closed space, or a surface intended to be deodorized or freshened, a malodor counteracting (MOC) composition in an amount sufficient to reduce, mask, eliminate or prevent malodor perception from the closed space or surface, wherein the MOC composition consists of a mixture of at least two ingredients selected from Group (I) compounds, at least one ingredient selected from Group (II) compounds, and at least two ingredients selected from Group (III) compounds, wherein the Groups (I) to (III) compounds are defined as follows:
    a) Group (I): aldehydes selected from at least two of the following sub-groups:
        Sub-group a): aldehydes consisting of a linear, saturated or unsaturated, aliphatic C7 chain, optionally substituted with up to six carbon atoms;
        Sub-group b): aldehydes consisting of a linear, saturated or unsaturated, aliphatic C8 chain, optionally substituted with up to five carbon atoms;
        Sub-group c): aldehydes consisting of a linear, saturated or unsaturated, aliphatic C9 chain, optionally substituted with up to four carbon atoms;
        Sub-group d): aldehydes consisting of a linear, saturated or unsaturated, aliphatic C10 chain, optionally substituted with up to three carbon atoms;
        Sub-group e): aldehydes consisting of a linear, saturated or unsaturated, aliphatic C11 chain, optionally substituted with up to two carbon atoms; or
        Sub-group f): aldehydes consisting of a linear, saturated or unsaturated, aliphatic C12 chain, optionally substituted with one carbon atom;
    b) Group (II): ketones of formula R2COR3, wherein R2 is an ethyl or methyl group and R3 is an aliphatic linear or branched, saturated or unsaturated carbon chain containing from 1 to 12 carbon atoms; and
    c) Group (III): primary alcohols selected from at least two of the following sub-groups:
        Sub-group g): alcohols consisting of a linear, saturated or unsaturated, aliphatic C6 chain, optionally substituted with up to seven carbon atoms;
        Sub-group h): alcohols consisting of a linear, saturated or unsaturated, aliphatic C8 chain, optionally substituted with up to five carbon atoms; or
        Sub-group i): alcohols consisting of a linear, saturated or unsaturated, aliphatic C10 chain, optionally substituted with up to three carbon atoms,
    wherein the aldehydes of Group (I) are present in a concentration of between 55 and 60% by weight, the ketone of Group (II) is present in a concentration of between 20 and 25% by weight and the primary alcohols of Group (III) are present in a concentration of between 20 and 25% by weight, all concentrations being relative to the total weight of the composition.

2. The method of claim 1, wherein the aldehydes of the MOC composition are selected from decanal, octanal, nonanal, 9-undecenal, (+−)-2,6-dimethyl-5-heptenal or (Z) 4 dodecenal.

3. The method of claim 1, wherein the ketone of the MOC composition is 2 octanone or 2-heptanone.

4. The method of claim 1, wherein the primary alcohols of the MOC composition are selected from decan-1-ol, hexan-1-ol, octan-1-ol, or (Z)-3-hexen-1-ol.

5. The method of claim 1, wherein each compound of the MOC composition is characterized by a vapor pressure above 4 Pa.

6. The method of claim 1, wherein the MOC composition is applied in the form of a deodorant or antiperspirant, an air freshener or a fabric softener or refresher.

7. The method of claim 1, wherein the MOC composition comprises at least three aldehydes of Group (I) compounds selected from at least three of Sub-groups a) to f).

8. The method of claim 1, wherein the MOC composition comprises three alcohols of Group (III) selected from Sub-Groups g) to i).

9. The method of claim 1, wherein the Group I aldehydes of the MOC composition includes a combination of octanal, nonanal and decanal.

10. The method of claim 1, wherein the Group III alcohols of the MOC composition include a combination of hexanol, octanol and decanol.

11. The method of claim 1, wherein the MOC composition consists of the combination of at least three aldehydes of Group (I) compounds selected from at least three of Sub-groups a) to f), at least one Group (II) compound, and at least two Group (III) compounds, wherein the aldehydes of Group (I) include a combination of octanal, nonanal and decanal, and wherein the alcohols of Group (III) include a combination of hexanol, octanol and decanol.

* * * * *